US005489637A

United States Patent [19]
Nguyen et al.

[11] Patent Number: 5,489,637
[45] Date of Patent: Feb. 6, 1996

[54] LOW TEMPERATURE FLEXIBLE DIE ATTACH ADHESIVE AND ARTICLES USING SAME

[75] Inventors: My N. Nguyen; Yuan Y. Chien, both of San Diego, Calif.

[73] Assignee: Johnson Matthey Inc, Valley Forge, Pa.

[21] Appl. No.: 392,602

[22] Filed: Feb. 22, 1995

Related U.S. Application Data

[60] Continuation of Ser. No. 68,794, May 27, 1993, abandoned, which is a division of Ser. No. 890,618, May 28, 1992, Pat. No. 5,250,600.

[51] Int. Cl.[6] ................................................ C08K 5/06
[52] U.S. Cl. ..................... 524/377; 524/381; 524/382; 528/361; 528/362; 528/363; 528/422
[58] Field of Search .............................. 524/377, 381, 524/382; 528/361, 362, 363, 422

[56] References Cited

U.S. PATENT DOCUMENTS

| | | | |
|---|---|---|---|
| 1,743,167 | 1/1930 | Styer. | |
| 2,895,270 | 1/1930 | Blaess | 53/21 |
| 3,586,926 | 6/1971 | Nakamura et al. | 257/682 |
| 3,595,900 | 7/1971 | Loudas et al. | 260/453 |
| 3,658,623 | 4/1972 | Grigat et al. | 156/331 |
| 4,280,885 | 7/1981 | Savery | 204/129 |
| 4,369,302 | 1/1983 | Ikeguchi et al. | 528/73 |
| 4,375,498 | 3/1983 | Le Minez et al. | 428/416 |
| 4,401,776 | 8/1983 | Munk | 523/443 |
| 4,552,690 | 11/1985 | Ikeguchi et al. | 252/512 |
| 4,604,452 | 8/1986 | Shimp | 528/422 |
| 4,608,434 | 8/1986 | Shimp | 528/422 |
| 4,699,888 | 10/1987 | Dumesnil et al. | 501/19 |
| 4,709,008 | 11/1987 | Shimp | 528/422 |
| 4,732,702 | 3/1988 | Yamazaki et al. | 252/512 |
| 4,740,343 | 4/1988 | Gaku et al. | 264/225 |
| 4,740,584 | 4/1988 | Shimp | 528/422 |
| 4,740,830 | 4/1988 | Ketley | 257/741 |
| 4,754,001 | 6/1988 | Blahak et al. | 525/437 |
| 4,785,075 | 11/1988 | Shimp | 528/422 |
| 4,831,086 | 5/1989 | Das et al. | 525/504 |
| 4,839,442 | 6/1989 | Craig, Jr. | 528/422 |
| 4,847,233 | 7/1989 | Shimp | 502/171 |
| 4,861,823 | 8/1989 | Qureshi | 524/606 |
| 4,902,752 | 2/1990 | Shimp | 525/390 |
| 4,918,157 | 4/1990 | Gardner | 528/322 |
| 4,931,545 | 6/1990 | Shimp et al. | 528/422 |
| 4,940,848 | 7/1990 | Shimp | 156/307.4 |
| 4,983,683 | 1/1991 | Shimp | 525/390 |
| 4,999,699 | 3/1291 | Christie et al. | 357/65 |
| 5,002,818 | 3/1991 | Licari et al. | 428/209 |
| 5,036,646 | 8/1991 | Makihara et al. | 53/432 |
| 5,037,692 | 8/1991 | Medney et al. | 428/252 |
| 5,056,296 | 10/1991 | Ross et al. | 53/478 |
| 5,068,309 | 11/1991 | Shimp | 528/211 |
| 5,114,003 | 5/1992 | Jackisch et al. | 206/204 |
| 5,143,785 | 9/1992 | Pujol et al. | 428/352 |
| 5,149,863 | 9/1922 | Shimp et al. | 560/301 |
| 5,150,195 | 9/1992 | Nguyen | 257/783 |
| 5,155,066 | 10/1992 | Nguyen | 437/209 |
| 5,162,574 | 11/1992 | Craig, Jr. | 560/301 |
| 5,186,880 | 2/1993 | Gaku et al. | 264/236 |
| 5,195,299 | 3/1993 | Nguyen | 53/428 |
| 5,215,860 | 6/1993 | McCormick et al. | 430/270 |
| 5,250,600 | 10/1993 | Nguyen | 524/377 |
| 5,261,157 | 11/1993 | Chang | 29/844 |
| 5,325,654 | 7/1994 | Juntunen et al. | 53/440 |
| 5,330,684 | 7/1994 | Emori et al. | 252/512 |
| 5,399,907 | 3/1995 | Nguyen et al. | 257/783 |

FOREIGN PATENT DOCUMENTS

| | | |
|---|---|---|
| 3423385 | 1/1985 | Germany . |
| 153338 | 9/1983 | Japan . |
| 2285968 | 12/1987 | Japan . |
| 3069883 | 3/1988 | Japan . |
| 9208247 | 5/1992 | WIPO . |
| 9316921 | 9/1993 | WIPO . |
| 9316987 | 9/1993 | WIPO . |
| 9317059 | 9/1993 | WIPO . |
| 9324564 | 12/1993 | WIPO . |
| 9406844 | 3/1994 | WIPO . |

OTHER PUBLICATIONS

D. A. Shimp, et al., "AroCy® Cyanate Ester Resin, Chemistry, Properties and Applications," Rhône–Poulenc, Inc.; Jan. 1990, pp. 1–36.

E. Grigat and R. Putter, "New Methods of Preparative Organic Chemistry VI—Synthesis and Reactions of Cyanic Esters," Agnew. Chem. Internat. Edit., vol. 6, Nov. 3, 1967, pp. 206–216.

Hi–Tek Polymers, "AroCy® L–10 Cyanate Ester Monomer," Oct. 1989.

Hi–Tek Polymers, "AroCy® Cyanate Ester Resins.".

Hi–Tek Polymers, "AroCy® F–40S Cyanate Easter Resin Solution," Oct. 1988, Apr. 1989.

Hi–Tek Polymers, "AroCy® B–10 Cyanate Ester Monomer," Oct. 1988.

Hi–Tek Polymers, "AroCy® B–40S Cyanate Ester Resin Solution," Oct. 1988.

Hi–Tek Polymers, "AroCy® B–50 Cyanate Ester Hard Resin," Oct. 1988.

Hi–Tek Polymers, "AroCy® M–10 Cyanate Ester Monomer," Oct. 1988.

Hi–Tek Polymers, "AroCy® M–30 Cyanate Ester Semisolid Resin," Oct. 1988.

Hi–Tek Polymers, "AroCy® M–50 Cyanate Ester Hard Resin," Oct. 1988.

Hi–Tek Polymers, "AroCy® T–30 Cyanate Ester Semisolid Resin," Oct. 1988.

Allied Signal Inc., "Primaset—PT Resins, Safety and Handling Bulletin," Mar. 20, 1992.

Allied Signal Inc., "Primaset—PT Resins."Allied–Signal Inc., "Primaset—PT Resins, Literature List."Tactix Perfromance Polymers, "XU–71787.02, XU–71787.07, Develop (List continued on next page.)

*Primary Examiner*—Edward Cain
*Attorney, Agent, or Firm*—Christie, Parker & Hale

[57] ABSTRACT

Described is a flexible adhesive formulation for bonding a semiconductor device to a flexible substrate and a flexible card containing a semiconductor device which can be processed in a computer.

20 Claims, 4 Drawing Sheets

OTHER PUBLICATIONS mental Polycyanate Resins for Advanced Composites and Adhesives."Sajal Das, "Phenol–Triazine (PT) Resin, A New Family of High Performance Thermosets" Cyanate Ester Symposium, Apr. 9–10, 1992.

D. A. Shimp and S. J. Ising, "Moisture Effects and their Control in the Curing of Polycyanate Resisn," Cyanate Ester Symposium, Apr. 9–10, 1992.

S. L. Simon and J. K. Gillham, "Cure of a Dicyanate Ester/Polycyanurate System," Cyanate Ester Symposium, Apr. 9–10, 1992.

Fraunhofer Institut fur Angewandte Materialforschung, "Polycyanurates and Their Modifications, State of the art and New Aspects," Gordon Research Conference on Thermoset, Jun. 1993.

Hi–Tek Polymers, "AroCy® Resins," Dec. 1988.

David Shimp and Mark Southcott, "Controlling Moisture Effects During the Curing of High $T_G$ Cyanate Ester/Aramid Composites," 38th International Symposium and Exhibition, May 10–13, 1993.

Rhône–Poulenc, "Specialty Resins—Reactive Rubber Tougheners for AroCy® Cyanate Ester Resins," Jan. 1991.

Rhône–Poulenc, "Specialty Resins—Pyrolysis of AroCy® Cyanate Esters."Rhône–Poulenc, "Specialty Resins—Quantative Determination of Residual Cyanate in Cured Homopolymers Via FTIR Analysis," Jan. 2, 1992.

Rhône–Poulenc, "Specialty Resins—Compatibility of Cyanate Esters with Aramid Reinforcements and Polyamide/Imide Substrates."Rhône–Poulenc, "Specialty Resins—AroCy® L–10 Cyanate Ester monomer," Sep. 1990.

Rhône–Poulenc, "Specialty Resins—AroCy® F–10 Cyanate Ester Monomer,"]Sep. 1990.

Rhône–Poulenc, "Specialty Resins—AroCy® M–20 Low Melt Viscosity Prepolymer," Sep. 1990.

Rhône–Poulenc, "Specialty Resins—AroCy® B–10 Cyanate Ester Monomer," Oct. 1990.

Rhône–Poulenc, "Specialty Resins—Toxicity of AroCy® Cyanate Ester."Rhône–Poulenc, "Specialty Resins—AroCy® M–10 Cyanate Ester Monomer," Sep. 1990.

Rhône–Poulenc, "Specialty Resins—AroCy® Cyanate Ester Resins."Rhône–Poulenc, "Specialty Resins—AroCy® Cyanate Ester Resins"list.

Rhône–Poulence, "Specialty Resisn—AroCy® F–40 S Cyanate Ester Resin Solution," Jul. 1990.

Rhône–Poulenc, "Specialty Resins—AroCy® B–30 Cyanate Ester Semisolid Resin."Rhône–Poulenc, "Specialty Resins—AroCy® B–40 S Cyanate Ester Resin Solution," Aug. 1990.

Rhône–Poulenc, "Specialty Resins—AroCy® B–50 Cyanate Ester Hard Resin," Sep. 1990.

Rhône–Poulenc, "Specialty Resins—AroCy® B–40S Cyanate Ester Resin Solution," Aug. 1990.

Rhône–Poulenc, "Specialty Resins—AroCy® M–30 Cyanate Ester Semisolid Resin," Sep. 1990.

Rhône–Poulenc, "Specialty Resins—AroCy® M–50 Cyanate Ester Hard Resin." Sep. 1990.

Rhône–Poulenc, "Specialty Resins—AroCy® Cyanate Ester Safety and Handling Bulletin," Sep. 1990.

Rhône–Poulenc, "Specialty Resins—Formulating AroCy® Cyanate Esters for Resin Transfer Molding Applications," Apr. 1991.

Rhône–Poulenc, "Specialty Resins—AroCy® Cyanate Ester Adhesives for Polyimide Flexible Circuitry," Jan. 1991.

Rhône–Poulenc, "Galvanic Corrosion of Carbon Fiber Composites," Jan. 1991.

Hi–Tek Polymers, "REX–378 Developmental Cyanate Ester Prepolymer."Uri Sela and Hans Steinegger, "Dispensing Technology—The Key to High–Quality, High–Speed Die Bondign," *Microelectronics Manufacturing Technology,* Feb. 1991, pp. 47–52.

Jack R. Christenson and David A. Shimp, "Improvements in Performance and Processing Using Cyanate Ester Blends and Alloys," Ultralloy '90, pp. 191–208.

Tony del Rasario, "JM 7000 Low Temperature Die Attach Material Qualification Report," Olin Interconnect Technologies, Dec. 10, 1992.

Malcolm L. White, et al., "Attaining Low Moisture Levels in hermetic Packages," *IEEE/Proc. IRPS,* 1982, pp. 253–259.

David P. Galloway and My N. Nguyen, "A New, Reliable Snap Cure Die Attach Adhesive," *Mat. Res. Soc. Symp. Proc.,* vol. 264, 1992, pp. 271–280.

Sue Oliver, et al., "Silver/Polymer Die Attach for Ceramic Package Assembly," 1992 IEPS meeting, Sep. 27–30, 1992.

My N. Nguyen and Michael B. Grosse, "Low Moisture Polymer Adhesive for Hermetic Packages," *IEEE Trans. on Components, Hybrids and Manufacturing Technology,* vol. 15, No. 6, Dec. 1992, pp. 964–971.

Richard H. Esters, "A Practical Approach to Die Attach Adhesive Selection," *Hybrid Circuit Technology,* Jun. 1991.

Tom Ramsey and gail Heinen, "Controlling Moisture in Ceramic Packages," *Semiconductor International,* Aug. 1988.

Mitsubishi Gas Chemical Company, Inc., "High Heat Resistant BT Resin—Bismaleimide–Triazine Resin," Fourth Edition, Sep. 1, 1984.

Sue Oliver, "Qualification Status and Extended Stressing of JM7000 Silver/Polymer Die Attach Adhesive for Ceramic Package Assembly," Jan. 12, 1993.

Hi–Tek Polymers, "AroCy® F–10 Cyanate Ester Monomer," Apr, 1989.

Hi–Tek Polymers, "AroCy® B–30 Cyanate Ester Semisolid Resin," Oct. 1988.

M. Bauer, J. Bauer and G. Kühn, "Kinetics and modelling of thermal polycyclotrimerization of aromatic dicyanates," Acta Polymerica 37 (1986), Nr. 11/12, pp. 715–719.

D. A. Shimp and W. M. Craig, Jr., "New Liquid Dicynate Mononer for Rapid Impregnation of Reinforcing Fibers," 34th Int'l SAMPE Symposium, 1989.

Hi–Tek Polymers, "AroCy Cyanate Ester Safety and Handling Bulletin, Arocy Safety and Handling".

Hans Steinegger, "Smart Cards: Bonding Technology at its Limits," Microelectronics Mfg. Tech., Dec. 1992, pp. 13–15.

Andrew Rosenbaum, "Smarter and Smarter", Electronics, Oct. 1991, 32D & 32 E.

Daniel Webb, "What Future is in the PC Cards?", Electronic Business, Nov. 4, 1991, p. 11.

"Japan Challenges Intel's Lead in Flash memories", attached chart World EPROM Market, Semiconductors.

Rhone–Poulenc, "Specialty Resins–Arocy Cyanate Ester Adhesives for Polyimide Flexible Circuitry", Jan. 1991.

Rhone–Poulenc, "Specialty Rubber Tougheners for Arocy Cyanate Ester Resins", Jan. 1991.

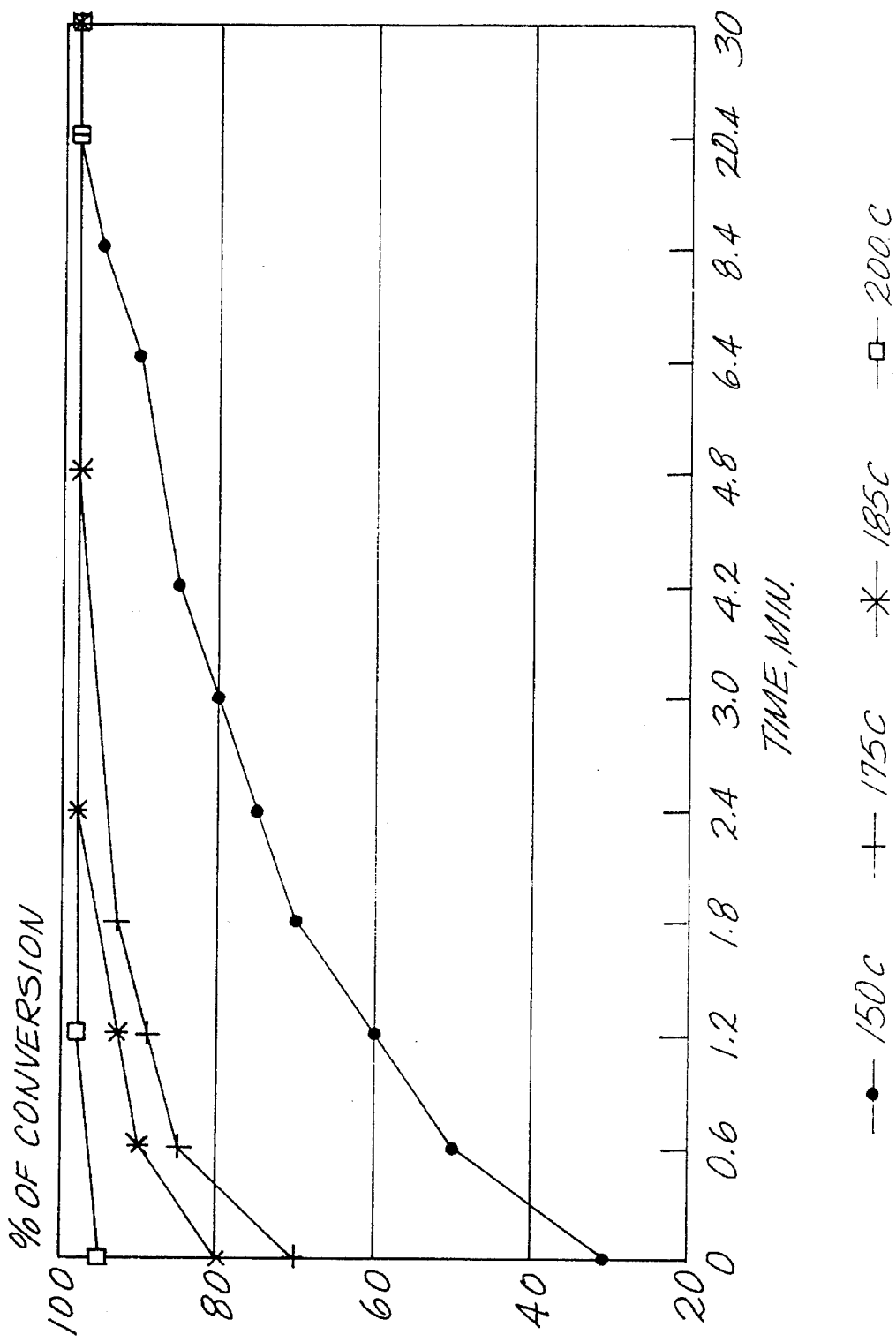

LOW TEMPERATURE FLEXIBLE DIE ATTACH ADHESIVE AND ARTICLES USING SAME

CROSS-REFERENCE TO RELATED APPLICATION

This application is a continuation of Ser. No. 08/068,794, now abandoned, filed May 27, 1993 which is a division of Ser. No. 07/890,618 filed May 28, 1992 now U.S. Pat. No. 5,250,600.

FIELD OF THE INVENTION

The present invention relates to a flexible die attach adhesive. The flexible die adhesive can be modified to be capable of developing very good adhesive strength at low curing temperatures. One embodiment of the invention relates to flexible card for processing in a computer that includes a semiconductor device enveloped therein adhered to a substrate by the aforementioned adhesive.

BACKGROUND OF THE INVENTION

As uses for semiconductor devices continue to increase there is a growing demand for adhesive compositions and formulations capable of securing semiconductor devices to substrates under a variety of conditions. The wide variety of applications using semiconductor devices sometimes require that such adhesive formulations be flexible where the device must be flexible and sometimes that the adhesive formulation be capable of developing very good adhesive strength at low curing temperatures so that significant stress is not imparted to the die and the curing conditions do not adversely affect other components. To improve workability, a modified adhesive formulation as described above but of low viscosity is also desirable.

One application employing semiconductor devices which is gaining increasing importance is in the field of cards to be processed in computers where such cards incorporate one or more semiconductor devices and are therefore able to store more information than magnetic cards. Such cards may be useful over a broad spectrum of applications including, for example, credit and telephone cards. These cards, which are referred to as "smart cards", must be thin and must be able to bend without breaking, i.e., the card and card components must be flexible.

Typically, "smart cards" are constructed of a material such as polyester reinforced with glass fibers and have enveloped within the card one or more semiconductor devices. Desirably, such devices should be secured within the card by a die attach adhesive which is flexible but which provides very good adhesive strength and does not impart stress to the die during curing. It is also important that the adhesive be capable of being cured at relatively low temperatures to facilitate fabrication of the cards without damage to the card or the semiconductor devices.

Cards including semiconductor devices enveloped therein are disclosed in an article by Hans Steinegger, Microelectronics Manufacturing Technology, pp. 13-15, December 1991; the disclosure of which is expressly incorporated herein by reference. As disclosed in the aforementioned article, the semiconductor devices have heretofore been bonded directly to a metal conductor or other substrate using an epoxy adhesive followed by encapsulation with epoxy resin. The obstacles to the production of such "smart cards" include problems arising in wire bonding because the basic material of the film is not as heat resistant as might be desired. It is pointed out in the article that for smart cards wire bonding must be performed at temperatures that do not exceed 180° C. It is apparent therefor that there is a need for a flexible die attach adhesive which is capable of being cured at relatively low temperatures but has very good adhesive strength.

SUMMARY OF THE INVENTION

Adhesive formulations have been proposed which are rapidly curing, i.e., are capable of being cured in under 5 minutes at 200° C. However, these formulations contain cyanate esters and are not flexible. The present invention provides a method of rendering cyanate esters flexible by reacting therewith at least one elastomeric and thermo plastic modifier from the group of hydroxyl (—OH), amine (NH) or epoxide reactive groups, or mixtures thereof by, for example, grafting such groups to cyanate molecular structures. Where flexible adhesive formulations with low viscosity are desired for better workability, etc., the cyanate esters are reacted with a polyhydroxyl polymer compound having the formula:

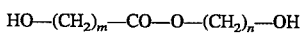

and/or

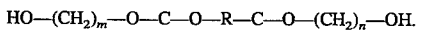

Advantageously, the polyhydroxyl polymer compound used has a molecular weight of between about 200 and about 5000 and contains at least two hydroxyl groups.

The cyanate ester may comprise an adhesive formulation suitable for bonding a semiconductor device to a substrate and may include a thermally and/or electrically conductive filler. The adhesive formulation may also include a curing catalyst.

In addition to the foregoing, the invention includes adhesive formulation for bonding a semiconductor device to a substrate, which comprises a reaction product of cyanate ester and the elastomeric modifier, as discussed above, having a low glass transition temperature of less than about 25° C. To impart rapid curability at low temperature, the adhesive may include an alkylphenol, a metal-containing curing catalyst, and/or silver in the form of flake or powder. Advantageously, the alkylphenol is nonylphenol, the metal-containing curing catalyst is from the group consisting of cobalt acetylacetonate and copper napthenate and the silver is present in amounts up to 90 wt. %. In one preferred embodiment the adhesive comprises the reaction product of 6 to 24 wt. % modifier and 4 to 16 wt. % cyanate ester, 0.01 to 0.06 wt. % metal-containing curing catalyst, 0.5 to 2 wt. % alkylphenol and up to 90 wt. % silver flake and/or powder. Where alkylphenol and/or metal containing catalyst are present as little as 4 to 20% silver may be sufficient. Where these curing catalysts are absent 60 to 90 wt. % silver may be needed to impart rapid curability to the adhesive formulation.

A novel card in accordance with the invention, for processing in a computer, comprises a semiconductor device enveloped within the card and adhered with a flexible adhesive to a substrate. The substrate is advantageously a flexible organic polymeric substrate and/or a lead frame or metal conductor. The adhesive comprises the reaction product of cyanate ester and modifier, as described above, having a glass transition temperature of less than about 25° C., and which may include an alkylphenol, a metal-containing curing catalyst and/or silver in the form of flake and/or powder.

BRIEF DESCRIPTION OF THE DRAWINGS

FIG. 4 is a graph illustrating % conversion of the polyhydroxyl polymer flexibilizer as a function of time and temperature.

DETAILED DESCRIPTION OF THE INVENTION

As has been previously explained, a flexible adhesive is needed for a number of applications where semiconductor devices with large surface areas are attached to flexible substrates, particularly where there is a significant difference between the thermal expansion coefficients of the silicon of the semiconductor device and the substrates. In such cases, a low-stress die attach adhesive is required for maximum performance. This is especially important where the semiconductor device is to be attached to lead frames, such as copper lead frames, and polymeric substrates such as polyester, polyamide films, etc.

If a conventional rigid adhesive such as epoxy referred to in the aforementioned Steinegger article is used in the above described applications, the thermally induced tensile stress imparted to the surface of the semiconductor die is so high that it usually results in a silicon fracture.

Figure 1:
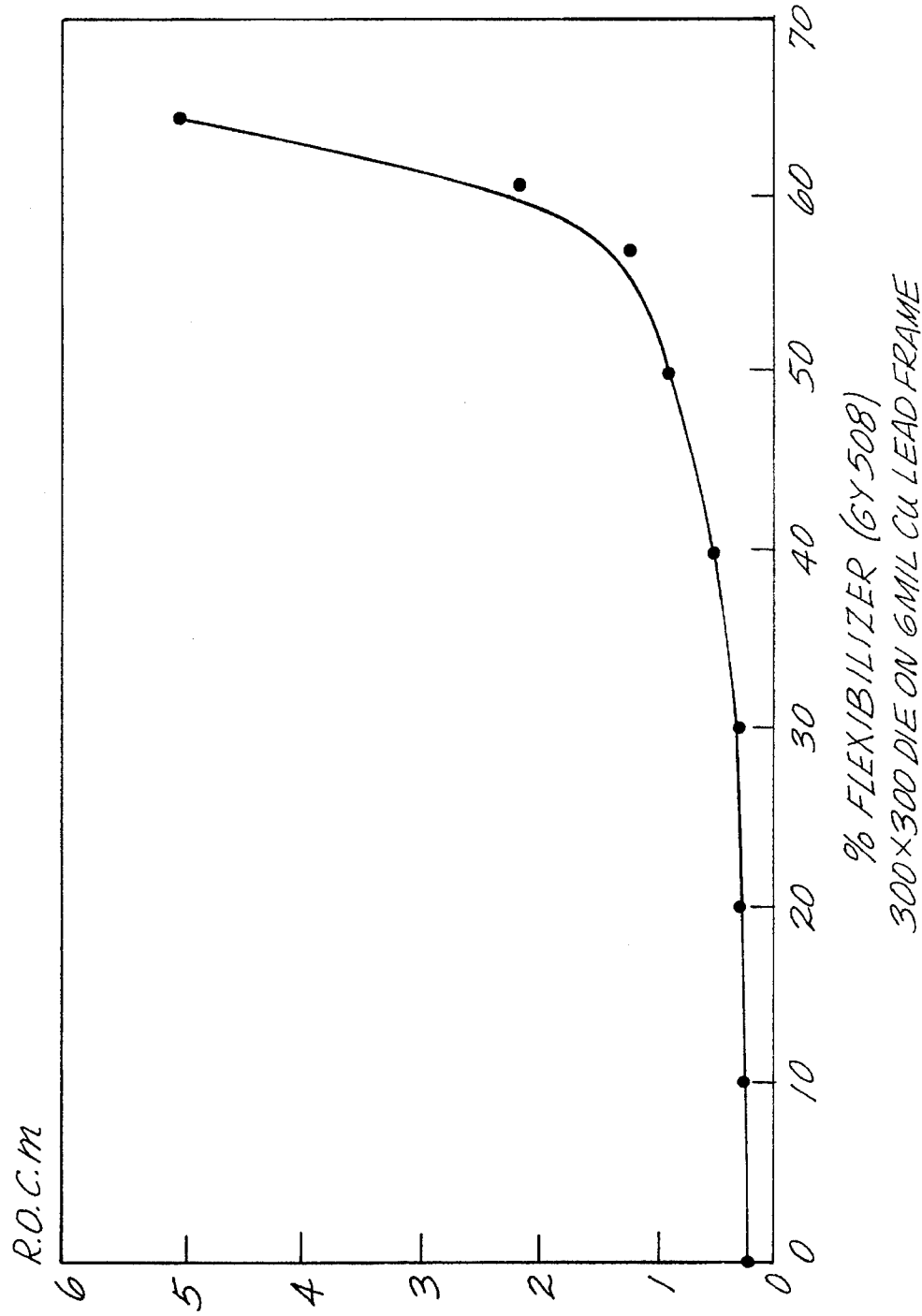
FIG. 1 is a graph showing the relationship between the percentage of modifier, i.e., flexibilizer and radius of curvature, ("ROC")

To assess the phenomenon involved it is necessary to measure the die stress. One such method is by determining the radius of curvature ("ROC"). A stress free die would be flat and would have a very large radius of curvature. The relationship between tensile stress imparted on the die surface and the radius of curvature is illustrated in FIG. 1. Since the tensile stress of silicon is about 100 MPa, an ROC value of about 1 meter or above is advantageous to eliminate silicon fracture with dies of customary size.

Die attach adhesive compositions including cyanate ester and silver do not give the flexible properties needed for the above applications. However, flexible properties can be achieved by reacting cyanate esters with at least one elastomeric and thermo plastic modifier from the group of hydroxyl (—OH), amine (NH) or epoxide reactive functional groups, or mixtures thereof by, for example, grafting such group to cyanate ester molecular structures.

To illustrate the foregoing, blends of low Tg, (Tg<25° C.), flexible epoxy and cyanate ester resin undergo the following reactions:

1) 3 R—O—C≡N ——>

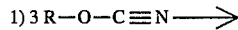

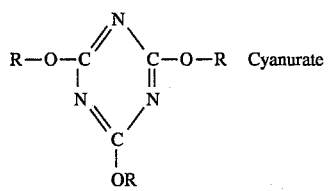

Cyanurate

2) R—O—C≡N + R'—CH——CH₂ ——>

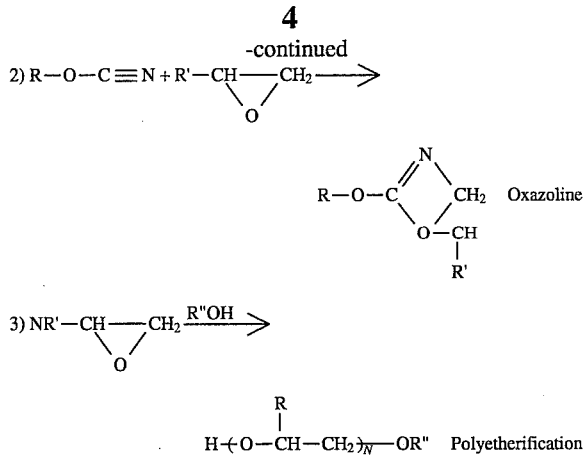

Figure 2:
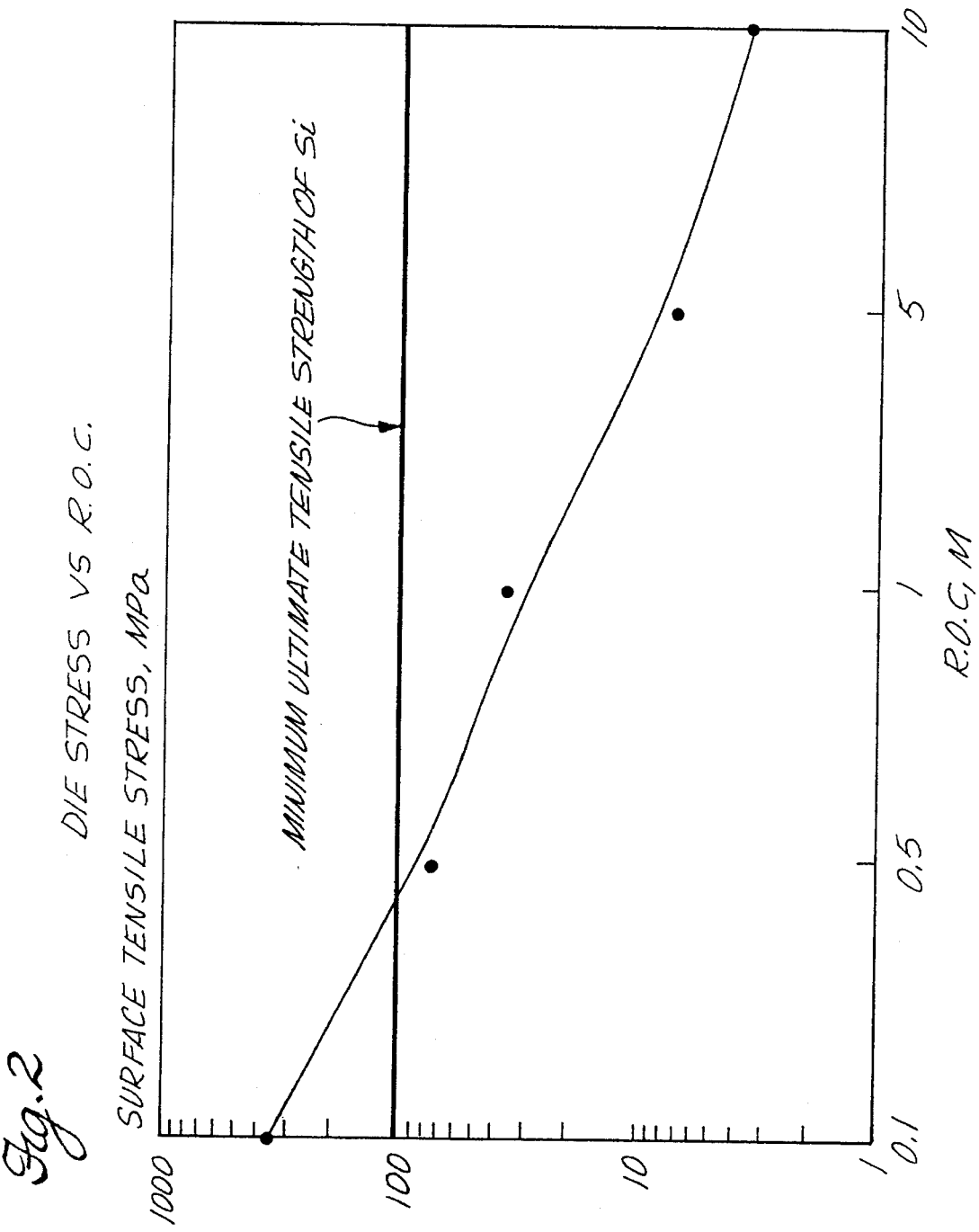
FIG. 2 is a graph of die stress against ROC.

The effect of flexible epoxy on ROC is shown in FIG. 2. As can be seen, a mixture of at least 50% epoxy gives acceptable performance and the cyanate ester in this mixture also acts as curing agent for the epoxy. However, at least about 15% cyanate ester is needed in the adhesive formulation to provide satisfactory curing in this system. Other elastomeric modifiers containing hydroxyl reactive groups, including hydroxyl terminated butadiene and butadiene-acrylonitrile copolymers, such as "HYCAR" sold by B.F. Goodrich and "VITEL-3600" which is a saturated copolyester resin with a Tg of −11° C., and polyhydroxyl polymer compounds are useful as well as amine functional groups such as polyurethane, elastomer, urethane acrylate, silicone imides, etc.

All of the foregoing modifiers have proven to be miscible with cyanate ester in the uncured state. During curing, the system is phase-separated, forming a co-continuous structure of hard and soft domains composed of cyanate ester-rich and elastomer-rich agglomerates. This system exhibits many advantageous properties, such as increased flexibility due to the soft modifier, while maximizing adhesive strength at high temperature.

The following are examples of some flexible adhesive formulations; with amounts in wt. %:

| EXAMPLES 1-4 | | | | |
|---|---|---|---|---|
| Composition | 1 | 2 | 3 | 4 |
| Cyanate Ester L10 | 20 | 20 | 20 | 20 |
| Silicone imide | | | | 20 |
| VITEL 3600 | 20 | | | |
| Urethane acrylate | | | 20 | |
| HYCAR HTBN | | 20 | | |
| Silver flake | 60 | 60 | 60 | 0 |
| Nonylphenol | 1.6 | 1.6 | 1.6 | 1.6 |
| ROC, m | 1.5 | 1.2 | 2.0 | 1.0 |
| Adhesion, 25 C, kg | 20 | 7.0 | 15 | 20 |
| 300 C | 1.5 | 0.5 | 1.5 | 1.5 |

| EXAMPLE 5 | |
|---|---|
| Composition | |
| Epoxy XB4122 | 14.57 |
| Arocy L10 | 9.71 |
| Cu Napthenate | 0.018 |
| Nonylphenol | 0.702 |
| Ag flake | 75.0 |
| Total | 100.0 |

EXAMPLE 5

Composition

| Curing Schedule | Die Shear, kg |
| --- | --- |
| cure 5 min, 125 C. | 5.6 |
| cure 1 hr, 125 C. | 10.0 |

Figure 3:
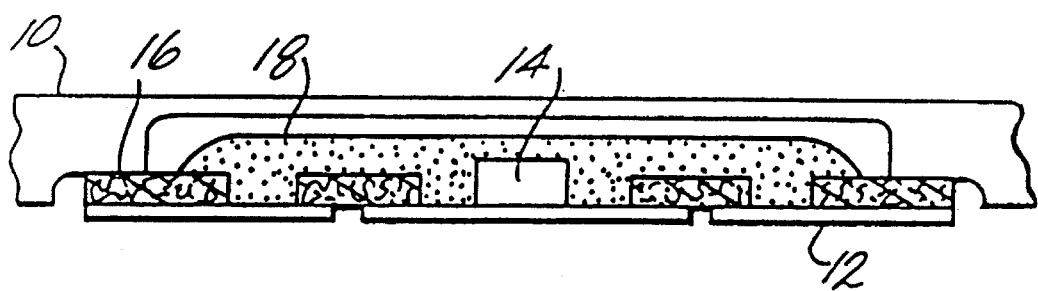
FIG. 3 is a schematic view partly in section of a card within which one or more semiconductor devices are enveloped and showing such devices bonded to a substrate.

A so-called "smart card" is shown in the schematic illustration depicted in FIG. 3. As can be seen, a card 10, usually made of plastic, includes a metal conductor 12 to which is bonded a semiconductor device 14. Glass fiber reinforced polyester pads 16 may be included and the entire device is encapsulated, such as within an epoxy resin 18. The epoxy resin may be ground flat to produce a thin plastic card.

The adhesive formulation of the present invention is especially suitable for bonding the semiconductor device to a substrate because it is capable of being cured at comparatively low temperatures of 100° to 150° C. and has very good adhesive strength while imparting low stress on the die. It is highly desirable for smart card application to employ a die attach adhesive capable of being cured at temperatures not substantially greater than about 150° C., preferably not greater than about 130° C. The die may be attached to a lead frame, such as a copper lead frame in which case the low temperature curing adhesive minimizes oxidation of the copper and thereby eliminates the need of nitrogen or other inert atmosphere such as is often used in curing ovens.

The following examples are of flexible adhesive compositions used to bond semiconductor devices suitable for smart card manufacture.

EXAMPLE 6

Flexible adhesive composition:

| Arocy L10 | 9.71% |
| --- | --- |
| XB4122 | 14.57% |
| Copper Napthenate, 8% Cu | 0.02% |
| Nonylphenol | 0.70% |
| Ag Flakes | 75.00 |

The cyanate ester Arocy L10 is available from Rhone-Poulenc of Louisville, Ky. The modified bisphenol epoxy resin such as XB 4122 or XUGY 376 is a flexible epoxy supplied by Ciba Geigy. The catalyst system is a solution of copper napthenate or copper acetylacetonate in nonylphenol. The silver flake has the same physical properties described in the previous examples. Adhesive strength results appear in Table I.

TABLE I

| ADHESION - LAP SHEAR | | |
| --- | --- | --- |
| Die Backside | Bore Si Die | Gold Coated Si Dies |
| 5 MIN CURE | | |
| Average Adhesion | 5.7 Kg | 6.6 Kg |
| Standard Deviation | 2.1 Kg | 3.9 Kg |
| Min Value | 3.2 Kg | 2.5 Kg |
| Max Value | 9.3 Kg | 14.9 Kg |
| Substrate: | Polyester film - Cu lead frame - Ni | |

TABLE I-continued

| ADHESION - LAP SHEAR | | |
| --- | --- | --- |
| Die Backside | Bore Si Die | Gold Coated Si Dies |
| | plated - Au flash | |
| Curing temperature: | 125 ± 5° C. | |
| Die size: | 5.5 × 4.5 mm - 217 × 177 mils. | |

The following is another example of a low curing adhesive formulation:

EXAMPLE 7

| Arocy L10 | 25 |
| --- | --- |
| Copper Napthenate, 8% | 0.04 |
| Nonylphenol | 1 |
| Ag flake | 75 |

The catalysts in the foregoing systems and in the systems hereinafter described may be copper napthenate or copper acetylacetonate, nonylphenol and silver. The formulation in Example 3 was cured at 100° C. for 15 minutes and exhibited an adhesive strength of over 30 Kg for a semiconductor die 150 mil² attached on a copper lead frame.

Where flexible adhesive formulations with low viscosity are desired, the cyanate esters are reacted with a polyhydroxyl polymer compound having the formula:

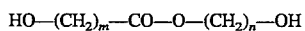

and/or

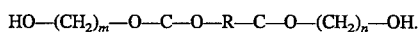

Preferred polyhydroxyl polymer compounds include polyhydroxyl polyester and polyhydroxyl polyether. Advantageously, the polyhydroxyl polymer compound used has a molecular weight of between about 200 and about 5000 and contains at least two hydroxyl groups. Such preferred low molecular weight polyhydroxyl polymer compounds result in low viscosity adhesive formulations of about 5 to 50 poise, the molecular weight being empirically related to viscosity. A molecular weight range of about 200 to about 5000 is preferred because below about 200 the material tends to be too volatile and above about 5000 the viscosity may be too high for processing conditions. Low viscosity adhesives which have improved workability enabling the formulation to be applied to a wide range of die sizes with varying substrate types, from flexible to rigid, and with reliable performance. Formulations employing polyhydroxyl polymers reacted with cyanate ester can be cured at temperatures between 30° C. to 200° C., as shown in FIG. 4, in the absence of a catalyst to form partially cross length (partially polymerized) B-stage, non-tacking films which can be subsequently hardened by heat to complete the polymerization in the actually applied process, such as during attaching of electronic devices to substrates. These formulations can be more rapidly cured, and at temperatures up to 200° C., in the presence of catalysts by either heat or UV to form adhesive formulations comprising soft rubber-like layers mass or layer and when combined with a rigid, hard, or elastic layer, both layers would be inseparable from one another. Of course, the compositions may be cured at higher temperatures with shorter curing time.

It has been found that adhesive formulations made from the reaction of polyhydroxyl polymers of compounds having the formula described above with cyanate ester possess a high adhesion strength over a wide range of curing temperatures and on different substrates. They also possess high temperature heat resistance of up to 350° C. and considerable flexibility, thereby providing low stress and low modulus characteristics which are useful with a wide range micro-electronic packages and devices. Suitable substrates for die attach adhesives include copper lead frames, printed circuit boards, laminates with "glob"-top coating for substrates varying from rigid to flexible.

The presently preferred low viscosity formulation comprises, in wt. %, 2–22% cyanate ester, 8–32% polyhydroxyl polymer compound, 0.01–0.06 wt. % metal-containing curing catalyst, up to 4.0% of an additive such as amorphous fume silica or clay, e.g., bentonite, for thixotropic behavior control, 0.5–2%, preferably 0.1–0.5%, alkylphenol and up to 90% silver flake and/or powder. The silver flake and/or powder preferably has a particle size within the range of 0.1–50 µm, a surface area of 0.1–2 m/g and a tap density of 2–6 g/cc.

Low viscosity flexible adhesive formulations of the present invention can be applied to a wide range of semiconductor die size and shape. For example, die sizes from 10 mil. to 700 mil. (0.4 mm to 0.28 mm) either square or rectangular may be employed. A substrate, which may be rigid or flexible, from material such as alumina, gold coatings or silver coatings, plain copper lead frames and of varying thicknesses from 4 mil. and above, may be used. The curing temperature can be from 30° C. to 300° C., but can be reduced with curing catalysts to 200° C. and the processing temperature may vary from 30° C. to 350° C., if required.

Other advantages of the low viscosity flexible adhesive formulation as described is that it is able to resist change even during high temperature thermal aging at 150° C.–185° C. and during thermal cycling from −60° C.–150° C. for at least 200 cycles. The formulations may be rapidly cured within 5 minutes at 200° C. or for longer times at lower temperatures.

The following Table II summarizes a number of examples of low viscosity flexible adhesive formulations employing polyhydroxyl polymer compounds described by their trade names, "Multron R-18", "Desmophen 1700, 1915 U, and 1652", respectively The material identified as "SD-2" is a bentonite clay additive which may be added to assist in improving thixotropic behavior, i.e., thixotropic characteristics. The physical properties of the examples in Table II are summarized in Table III.

TABLE II

| COMPO-SITION | 8 | 9 | 10 | 11 | 12 | 13 | 14 |
|---|---|---|---|---|---|---|---|
| Cyanate Ester | 14.875 | 14.875 | 11.85 | 14.875 | 11.8 | 17.375 | 14.75 |
| Multron R-18 | 14.875 | | | | | 17.375 | |
| Desmophen 1700 | | 14.875 | | | 17.7 | | |
| Desmophen 1915U | | | 7.9 | | | | 2.95 |
| Desmophen 1652 | | | | 14.875 | | | 11.8 |
| Silver Flake | 70 | 70 | 80 | 70 | 70 | 65 | 70 |
| Cobalt Naphthenate | 0.25 | 0.25 | 0.25 | 0.25 | 0.25 | 0.25 | 0.25 |
| SD-2 | | | | | | | 0.25 |

TABLE III

| Composition | 8 | 9 | 10 | 11 | 12 | 13 | 14 |
|---|---|---|---|---|---|---|---|
| R.O.C. m. | 1.4 | 1.6 | 1.5 | 1.4 | 4.5 | 1.5 | 1.9 |
| Die Shear Adhesion (kg) 25° C. | >50 | >50 | >50 | >50 | 47 | >50 | >50 |
| Die Shear Adhesion (kg) 300° C. | 2.5 | 2.2 | 2.0 | 2.4 | 1.5 | 2.5 | 2.4 |
| Tg. | 60° C. | 60° C. | 60° C. | — | — | — | — |
| wt. loss (TGA) at 300° C. | 0.7 | 0.8 | 1.1 | 0.5 | 1.3 | 0.5 | — |

To illustrate that the shear strength of the formulations described in Table II is maintained and does not degrade over time the composition of Example 8 was subjected to adhesion stability testing to compare die share against aging time. The average results of ten samples are reported in Table IV. For this test, the substrate used was a copper lead frame of 6 mil. thickness, a curing temperature of 150° C., an aging temperature of 150° C., and a die size of 5.08×5.08 mm–200×200 mil.

TABLE IV

| TIME | DIE SHEAR (kg) 25° C. | DIE SHEAR (kg) 300° C. |
|---|---|---|
| 15 Minutes | >50 | 2.5 |
| 30 Minutes | >50 | 2.4 |
| 24 Hours | >50 | 2.5 |
| 72 Hours | >50 | 2.4 |
| 168 Hours | >50 | 2.5 |
| 264 Hours | >50 | 2.5 |
| 600 Hours | >50 | 2.6 |

In order to determine whether the die stress remains at acceptable levels for the polyhydroxyl polymer containing adhesive formulations, test of flexibility tests were run to determine the radius of curvature change, if any, over time. The average results of ten samples of the Example 8 composition are reported in Table V which summarizes the tests conducted on the same substrate at the same curing and aging temperature described in connection with the tests reported in Table IV but with different die size. The die size for these tests were 15.24×15.24 mm–600×600 mil.

TABLE V

| TIME | R.O.C. (m) |
|---|---|
| 30 Minutes | 1.4 |
| 72 Hours | 1.5 |
| 120 Hours | 1.5 |
| 288 Hours | 1.45 |
| 360 Hours | 1.45 |

It is apparent from the foregoing that various changes and modifications may be made without departing from the spirit of the invention. Accordingly, the scope of the invention should be limited only by the appended claims wherein

What is claimed is:

1. A method of making a cyanate ester flexible which comprises reacting the cyanate ester with at least one flexibilizer having a glass transition temperature less than about 25° C., and comprising at least one member from the group consisting of compounds containing hydroxyl groups having a molecular weight of about 200 to 5000, compounds containing amine and compounds containing epoxide reactive functional groups, or mixtures thereof, to produce a formulation having a viscosity of about 5 to 50 poise and a radius of curvature of about 1 meter or more.

2. A method of making a cyanate ester flexible which comprises reacting the cyanate ester with at least one flexibilizer having a glass transition temperature less than about 25° C. comprising at least one polyhydroxyl polymer compound having a molecular weight of about 200 to about 5000 from the group of polyhydroxyl polymer compounds within at least one of the following formulas:

HO—(CH$_2$)$_m$—CO—O—(CH$_2$)$_n$OH, and

HO—(CH$_2$)$_m$—O—C—O—R—C—O—(CH$_2$)$_n$—OH to produce a formulation having a viscosity of about 5 to 50 poise and a radius of curvature of about 1 meter or more.

3. A method according to claim 2 wherein said polyhydroxyl polymer compound is one from the group consisting of polyhydroxyl polyesters and polyhydroxyl polyethers.

4. A method according to claim 2 wherein said cyanate ester further includes a metal containing co-curing catalyst.

5. A method of rendering a cyanate ester flexible which comprises adding to the cyanate ester at least one polyhydroxyl polymer compound having a glass transition temperature less than about 25° C. and a molecular weight range of about 200 to about 5000 within at least one of the following formulas:

HO—(CH$_2$)$_m$—CO—O—(CH$_2$)$_n$—OH and

HO—(CH$_2$)$_m$—O—C—O—R—C—O—(CH$_2$)$_m$—OH or mixtures thereof, and grafting such polymer to the cyanate ester molecular structure.

6. A method according to claim 1 wherein said cyanate ester is reacted with an amine reactive functional group.

7. A method according to claim 1 wherein said cyanate ester is reacted with an epoxide reactive functional group.

8. A method according to claim 1 wherein said method comprises reacting cyanate ester with an amine reactive functional group.

9. A method according to claim 1 wherein said method comprises reacting cyanate ester with an epoxide reactive functional group.

10. A method of making a cyanate ester flexible which comprises reacting 4 to 16 wt. % cyanate ester with 6 to 24 wt. % of at least one flexibilizer having a glass transition temperature less than about 25° C. containing one reactive functional group from the group of hydroxyl, amine and epoxide reactive functional groups, or mixtures thereof, wherein flexibilizers containing hydroxyl reactive functional groups have a molecular weight in the range of about 200 to about 5000.

11. A method according to claim 1 wherein said cyanate ester comprises an adhesive formulation suitable for bonding a semiconductor device to a substrate and further comprises a thermally and/or electrically conductive filler.

12. A method according to claim 2 wherein said filler comprises silver.

13. A method according to claim 2 wherein said adhesive formulation further comprises a curing catalyst.

14. A method according to claim 3 wherein said adhesive formulation further comprises an alkylphenol.

15. A method according to claim 1 wherein said cyanate ester comprises an adhesive formulation suitable for bonding a semiconductor device to a substrate and further comprises a thermally and/or electrically conductive filler.

16. A method according to claim 15 wherein said filler comprises silver.

17. A method according to claim 15 wherein said adhesive formulation further comprises a curing catalyst.

18. A method according to claim 5 wherein said cyanate ester comprises an adhesive formulation suitable for bonding a semiconductor device to a substrate further comprising adding a thermally and/or electrically conductive filler.

19. A method according to claim 18 wherein said filler comprises silver.

20. A method according to claim 18 further comprising adding a curing catalyst.

* * * * *

UNITED STATES PATENT AND TRADEMARK OFFICE
CERTIFICATE OF CORRECTION

PATENT NO. : 5,489,637　　　　　　　　　　　　　　Page 1 of 3
DATED : February 6, 1996
INVENTOR(S) : My N. Nguyen; Yuan Y. Chien It is certified that error appears in the above-indentified patent and that said Letters Patent is hereby corrected as shown below:

On the Title Page, Item [56], References Cited:
U.S. PATENT DOCUMENTS
　　　　Column 1, line 30, change
　　　　　　"4,999,699 3/1291 Christie et al..357/65" to
　　　　　-- 4,999,699 3/1991 Christie et al..357/65 --.

OTHER PUBLICATIONS

Column 2, line 11, in the "Hi-Tek Polymers"
　　　　　reference change
　　　　　　"Cyanate Easter Resin Solution," to
　　　　-- Cyanate Ester Resin Solution --.

Column 2, lines 29-31 and page 2, column 1,
　　　lines 1-4, list the four references cited as
　　　follows:

-- Allied Signal Inc., "Primaset—PT Resins.

Allied Signal Inc., "Primaset—PT Resins,
　　　　Literature List."

UNITED STATES PATENT AND TRADEMARK OFFICE
CERTIFICATE OF CORRECTION

PATENT NO. : 5,489,637             Page 2 of 3

DATED : February 6, 1996

INVENTOR(S) : My N. Nguyen; Yuan Y. Chien

It is certified that error appears in the above-indentified patent and that said Letters Patent is hereby corrected as shown below:

Tactix Performance Polymers, "XU-71787.02, XU-71787.07, Developmental Polycyanate Resins for Advanced Composites and Adhesives.

Sajal Das, "Phenol—Triazine (PT) Resin, A New Family of High Performance Thermosets," Cyanate Ester Symposium, Apr. 9-10, 1992. --.

Page 2, column 1, line 12, in the "Frauenhofer Insitut" reference, change "State of the art" to -- State of the Art --.

Page 2, column 1, line 29, in the "Rhône-Poulenc" reference, change "Cyanate Ester monomer" to -- Cyanate Ester Monomer --.

Page 2, column 1, line 31, before "Sep. 1990" delete the bracket.

Page 2, column 2, line 8, before "Microelectronics" change "Bondign"" to -- Bonding" --.

Page 2, column 2, line 17, before "Packages" change "hermetic" to -- Hermetic --.

Page 2, column 2, line 30, change "gail Heinen" to -- Gail Heinen --.

UNITED STATES PATENT AND TRADEMARK OFFICE
CERTIFICATE OF CORRECTION

PATENT NO. : 5,489,637
DATED : February 6, 1996
INVENTOR(S) : My N. Nguyen; Yuan Y. Chien It is certified that error appears in the above-indentified patent and that said Letters Patent is hereby corrected as shown below:

```
Column 10, line 18, change "claim 2" to -- claim 11 --.
Column 10, line 21, change "claim 2" to -- claim 11 --.
Column 10, line 23, change "claim 3" to -- claim 13 --.
```

Signed and Sealed this

Fifth Day of November, 1996

Attest:

BRUCE LEHMAN

*Attesting Officer*   Commissioner of Patents and Trademarks

UNITED STATES PATENT AND TRADEMARK OFFICE
CERTIFICATE OF CORRECTION

PATENT NO. : 5,489,637
DATED : February 6, 1996
INVENTOR(S) : My N. Nguyen; Yuan Y. Chien It is certified that error appears in the above-indentified patent and that said Letters Patent is hereby corrected as shown below:

```
      On the title page, item [56], change:
        "5,037,692  8/1991  Medney et al....428/252" to
     -- 5,037,691  8/1991  Medney et al....428/252 --.
```

Page 2, column 1, line 50, in the "Rhône-Poulenc" reference
change "AroCy®B-40S" to -- AroCy®M-40S --.

Signed and Sealed this

Twenty-fourth Day of December, 1996

Attest:

BRUCE LEHMAN

Attesting Officer

Commissioner of Patents and Trademarks